(12) United States Patent
Royse et al.

(10) Patent No.: US 7,329,266 B2
(45) Date of Patent: Feb. 12, 2008

(54) SURGICAL CLAMPS

(75) Inventors: Alistair Royse, Eltham (AU); Brett Hamilton, Tooradin (AU); David Berry, North Ringwood (AU); Michael Kerr, Ivanhoe (AU)

(73) Assignee: Research Surgical Pty Ltd, Victoria (AU)

( * ) Notice: Subject to any disclaimer, the term of this patent is extended or adjusted under 35 U.S.C. 154(b) by 35 days.

(21) Appl. No.: 10/521,422

(22) PCT Filed: Jul. 26, 2002

(86) PCT No.: PCT/AU02/00996

§ 371 (c)(1),
(2), (4) Date: Sep. 23, 2005

(87) PCT Pub. No.: WO03/011150

PCT Pub. Date: Feb. 13, 2003

(65) Prior Publication Data

US 2006/0129170 A1    Jun. 15, 2006

(51) Int. Cl.
*A61B 17/08* (2006.01)
(52) U.S. Cl. .................................. 606/158
(58) Field of Classification Search ............ 606/158, 606/151, 157; 251/10
See application file for complete search history.

(56) References Cited

U.S. PATENT DOCUMENTS

D234,204 S    1/1975  Miller et al.
4,112,944 A *  9/1978  Williams .................. 604/244
4,346,869 A *  8/1982  MacNeill .................. 251/10
4,390,019 A *  6/1983  LeVeen et al. ............ 606/158
4,550,729 A * 11/1985  Cerwin et al. ............ 606/158
4,835,824 A *  6/1989  Durham et al. ............ 24/339
5,676,676 A * 10/1997  Porter ...................... 606/158

FOREIGN PATENT DOCUMENTS

CA    2183998 A    2/1998
SU     735245      5/1980

OTHER PUBLICATIONS

International Search Report for PCT/AU2002/000996; ISA/AU; Mailed: Sep. 25, 2002.

* cited by examiner

*Primary Examiner*—Michael J. Hayes
*Assistant Examiner*—Christina Gettman
(74) *Attorney, Agent, or Firm*—Harness, Dickey & Pierce, PLC

(57) ABSTRACT

An arterial clamp has opposed clamping posts arranged to lie at opposite sides of an artery to clamp the artery between opposed clamping faces of the posts. The posts are carried by a pair of arms pivotally movable one relative to the other to move the posts into clamping relationship with the artery. A ratchet device releasably locks the arms in a selected clamping position. The clamp including posts, arms, and ratchet device is formed as a one-piece plastics moulding.

8 Claims, 3 Drawing Sheets

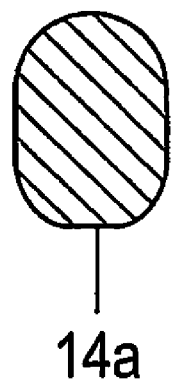
FIG. 5
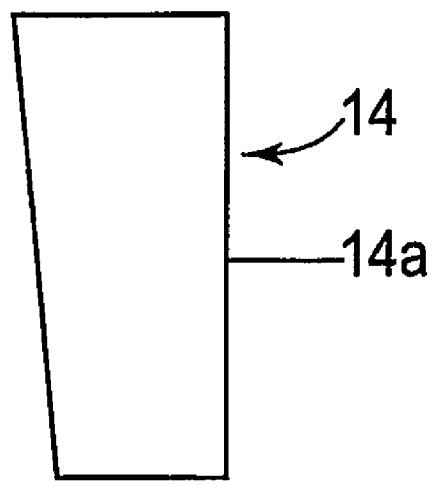
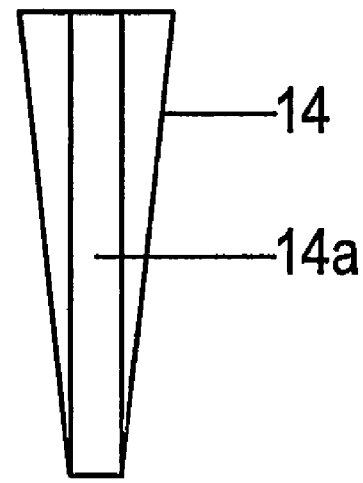
FIG. 4
FIG. 3

SURGICAL CLAMPS

CROSS-REFERENCE TO RELATED APPLICATIONS

This Application is a U.S. National Stage of International Application No. PCT/AU2002/000996 filed 26 Jul. 2002 and published in English as WO 03/011150 A1 on 13 Feb. 2003. The disclosure(s) of the above application is incorporated herein by reference.

The present invention relates to clamps for surgical use, both human and veterinary. More particularly the invention relates to clamps for occluding coronary arteries and other arteries used to perform bypass grafts to coronary arteries, being suitable also for use with other vessels or tube-like structures of generally similar dimensions in humans or animals to compress the structure to prevent passage of blood or other fluid.

When performing "off pump" coronary artery bypass surgery (CAGS), the intention is to perform the bypass without stopping the heart. Therefore it is necessary to occlude the coronary artery by means of clamps on either side of a small incision made in the artery to which the bypass artery conduit will be sewn. Accordingly blood flow is temporarily prevented to part of the heart whilst the grafting is being performed. Subsequently, the clamps are removed and the coronary artery then receives supplementary blood flow via the graft.

One form of existing clamp for this purpose is a plastic derivation of the traditional metal "bulldog" clamp but smaller and lighter. It works by being opened with finger pressure and closed by the inherent resilience of the material. Frequently, the clamping pressure provided is not sufficient to adequately control blood flow. Also it is relatively long, making it difficult to fit easily within the stabilizing arms of an associated retractor device. It can become displaced perpendicularly to the heart such that it impedes the vision of the surgeon as well as catching the suture thread during grafting. Metal versions of the clamp also suffer from disadvantages due to their weight which results in counter-forces existing due to their inertia when attached to the moving heart. Consequently, they also frequently dislodge. Their greater size makes placement in confined spaces even more difficult.

Existing clamps for use on the conduits (arteries to be used as grafts) tend either to be the metal version of the "bulldog" clamp or a plastic spring-loaded clamp. The weight of the metal clamps results in substantial "drag" on the conduit during grafting which adds to the difficulty of the graft. The plastic spring-loaded clamp comprises spring-loaded vice-like jaws and is larger and its bulk makes it less suitable in confined spaces, resulting in additional and redundant lengths of conduit being required where more than one graft is performed for each conduit (sequential anastomoses).

According to the present invention, there is provided a clamp for surgical use comprising opposed clamping members pivotally movable one relative to the other between an open condition and a closed clamping condition, and a ratchet device operative during closing movement to retain the clamping members in a selected, closed, clamping condition.

Advantageously, the ratchet device comprises a series of ratchet teeth in an arcuate array centered on the axis of pivotal movement of the clamping members, and a ratchet tooth movable with one of said clamping members upon pivotal movement of that clamping member relative to the other clamping member to move along the array of ratchet teeth to be retained thereby in a selected clamping position.

A particularly preferred embodiment of the invention comprises a pair of arms pivotally interconnected at adjacent ends for pivotal movement between an open configuration in which the arms define a V-shaped configuration and a closed configuration in which the arms are approximately parallel, one of the arms having at its end remote from the pivot the ratchet tooth and the other arm having on its end remote from the pivot a limb formed with said array of ratchet teeth with which the ratchet tooth engages upon closure of the two arms, each of the clamping members being carried by a respective one of the two arms.

Advantageously, the clamping members are of post-like form extending in a plane directed transversely to a plane containing the arms of the clamp.

Particularly advantageously, clamping faces of the opposed clamping members are inclined one relative to the other so as to converge in a direction towards tip portions of the clamping members. In one embodiment, the clamping faces are each inclined to the perpendicular by an angle of approximately 4 to 6° so as to converge at an included angle of approximately 8° to 12°. This convergence facilitates retention of the clamp.

Advantageously, the clamp is formed as a one-piece plastics moulding with the pivot being formed by a hinge consisting of a flexible web of plastics material interconnecting the adjacent ends of the two arms.

According to another aspect of the invention, there is provided an arterial clamp comprising opposed clamping posts arranged to lie at opposite sides of an artery to clamp the artery between opposed clamping faces of the posts, the posts being movable into clamping relationship with the artery by arcuate movement of one post relative to the other about a hinge zone, and a device for releasably locking the clamping posts in a selected clamping position, the clamp being formed as a one-piece plastics moulding.

An embodiment of the invention will now be described, by way of example only, with reference to the accompanying drawings, in which:

FIG. 3 is a detail looking in the direction of arrow B in FIG. 1 and showing a clamping post;

FIG. 4 is a detail view of the clamping post at right angles to the view of FIG. 3; and FIG. 5 is a transverse section through the clamping post.

Figure 1:
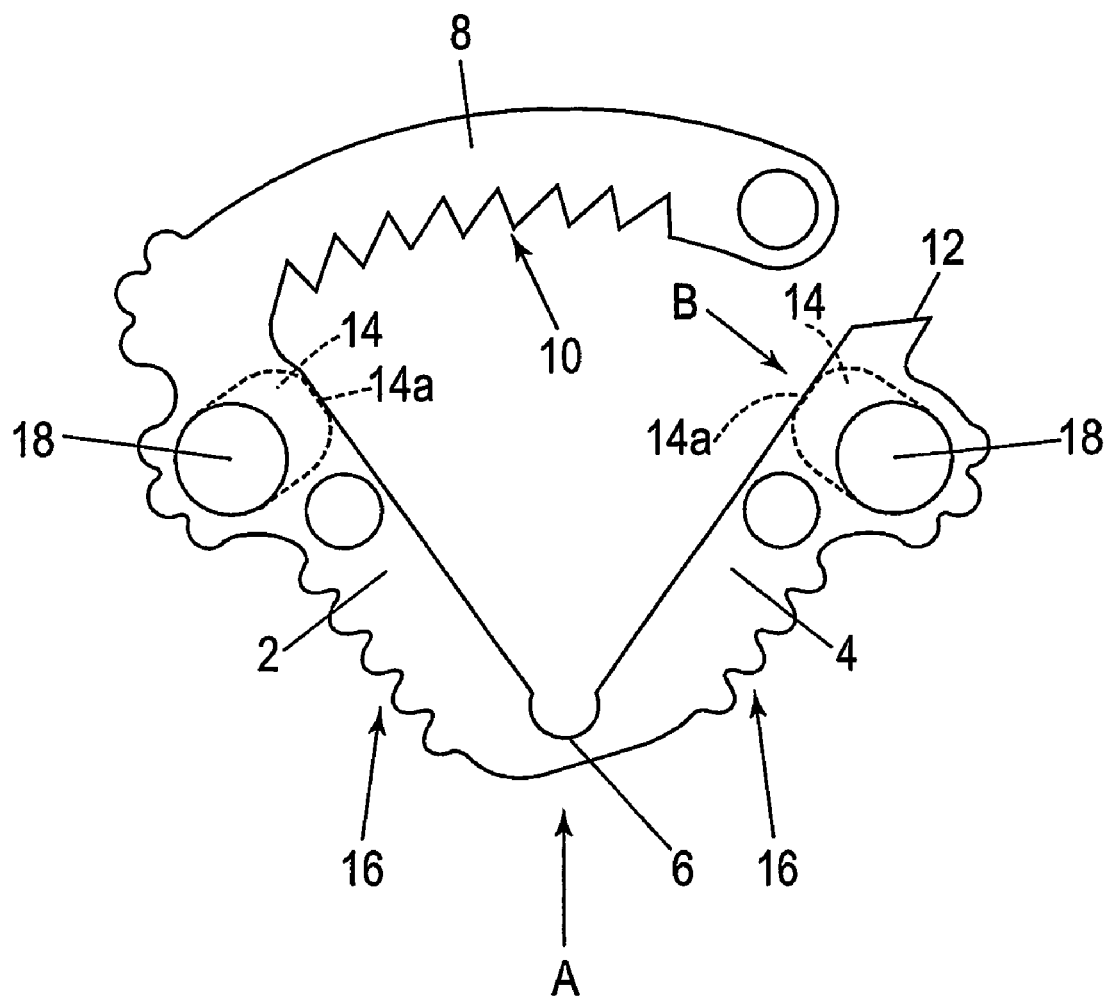
FIG. 1 is a plan view of a clamp in accordance with the preferred embodiment of the invention.
Figure 2:
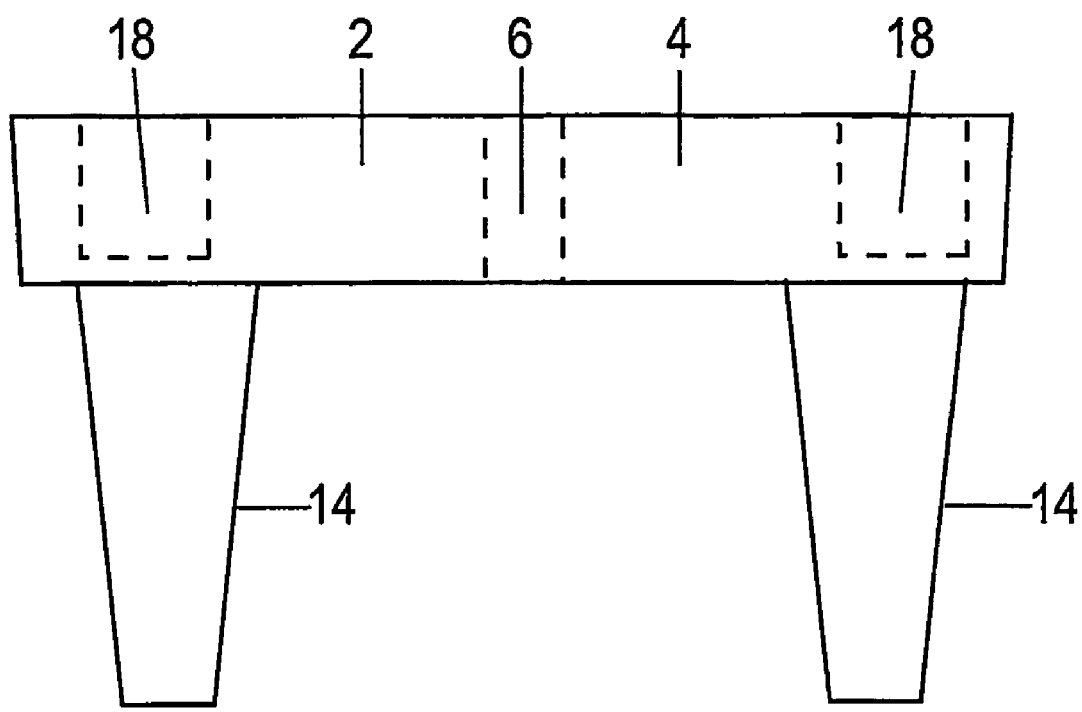
FIG. 2 is a schematic view of the clamp looking in the direction of arrow A in FIG. 1.

An arterial clamp in accordance with the preferred embodiment of the invention is formed as a one-piece moulding in a suitable plastics (for example, homopolymer polypropylene or acetal copolymer) and consists of opposed arms 2, 4 pivotally connected at one end by a hinge 6 formed by a flexible web of the plastic material so as to be movable from a substantially V-shaped open configuration as shown in FIG. 1, to a closed clamping configuration in which the arms 2, 4 are approximately parallel. The outer end of the arm 2 is formed with a projecting limb 8 having on its inner face a set of ratchet teeth 10, the teeth 10 extending along a curved path centered on the pivotal axis of the hinge 6 connecting the two arms 2, 4. The outer end of the arm 4 is formed with a ratchet tooth 12 to co-operate with the ratchet teeth 10. Each of the arms 2, 4 is formed with a clamping post 14 projecting substantially perpendicular to the plane of the arms 2, 4, the posts 14 forming the actual clamping members of the clamp. In use, the two posts 14 lie on opposite sides of the artery and to clamp the artery the two arms 2, 4 are closed by pivotal movement about the hinge 6 with the ratchet tooth 12 at the end of the arm 4 moving along the ratchet teeth 10 on the projecting limb 8 until the required clamping condition has been attained, with the arms 2, 4 being positively held in that condition by the one way action of the ratchet teeth.

The clamp is able to be positioned, manipulated, and closed by forceps or the like engaging the outer sides of the two arms 2, 4 for which purpose the sides are preferably provided with a series of small projections 16 along their length to facilitate retention by the forceps. The arms 2, 4 are each also provided with holes 18 for receiving the tips of the forceps, to provide further versatility.

With the clamp described above, the surgeon can apply whatever clamping pressure is considered appropriate to stop fluid flow and once applied, that pressure will be maintained due to the locking effect provided on the two arms 2, 4 by the ratchet action provided by the interengaging teeth 10, 12. To release the clamp, all that is necessary is to displace the projecting limb 8 laterally out of the plane of the second arm 4 to thereby release the teeth 10 from engagement with the tooth 12. This can readily be achieved due to the inherent flexibility of the plastics material.

In the embodiment shown, the two clamping posts 14 are of tapered shape, narrowing towards their distal end. The clamping face 14a of each post 14 is a planar face and the post 14 is elongated in transverse cross section, with the elongation serving to maximise the resistance to deflection of the clamping post 14 under the clamping pressures. The clamping face 14a may be formed with a series of very small ridges or depressions to facilitate improved grip between the face and the tissue. The distal or tip end of each clamping post 14 may also be provided with a small lip to aid retention. Although the clamping posts 14 may extend in a plane at right angles to the plane of the arms 2, 4, alternatively they may be positioned in a plane inclined out of that 90° plane and away from the ratchet limb 8 so that the ratchet limb 8 is "lifted" a little further away from the zone of clamping of the two clamping posts 14.

Although in the embodiment illustrated, the clamping faces 14a of the two posts 14 are substantially parallel and perpendicular to the plane of the arms 2, 4, we have determined that it is particularly advantageous for the two clamping faces to converge in a direction towards their tip ends. Typically, each clamping face is inwardly inclined relative to the perpendicular by approximately 4 to 6° to provide an included angle of convergence between the two clamping faces of approximately 8 to 12°. This convergence although relatively small causes greater clamping force to be exerted at the tip portions and significantly facilitates retention on the artery. In the fully closed condition of the clamp the tip ends of the posts 14 engage at their clamping faces and deflect slightly.

By way of illustration, the length of the clamp from the hinge 6 to the outer side of the ratchet limb 8 is about 10 mm which makes the clamp significantly smaller than the existing forms of clamp previously discussed, this substantial size reduction being obtained due to the basic shape as illustrated incorporating the locking ratchet mechanism. Accordingly, the ratchet mechanism not only allows the clamping force to be controlled and maintained it is also used to achieve a substantial reduction in overall length which allows for easier positioning in confined spaces.

The shape of the clamp makes it much less prone to projecting perpendicular to the surface of the heart and so less prone to catching the suture material during the construction of the anastomosis. The plastic construction reduces the weight substantially in comparison to metal and therefore the clamp will easily move with the heart and so not be prone to dislodgement consequent on heart motion; nor will this drag the conduit excessively if used to occlude the conduit.

It is envisaged that the clamp would be single use only and not intended for re-cleaning and re-sterilization. In fact re-sterilization would be very difficult due to the presence of the depressions/holes provided to allow the clamp to be grasped by forceps or other devices to allow positioning and tightening, preventing adequate cleaning and removal of blood from the clamp.

It would be intended that two such clamps would be used to occlude a single coronary artery and a further one for the conduit. Within each operation, the clamps could be used on more than one coronary artery.

The size of coronary arteries grafted ranges from 1.0 mm to 2.5 mm in diameter, with most being 1.5-2.0 mm. The size of conduits usually ranges from 1.75 mm to 3-4 mm. These sizes would be relatively similar to many arteries or veins used in other forms of vascular or plastic surgery where arteries are being joined together or transplanted. In other disciplines of surgery, arteries of this size are frequently encountered and sometimes, temporarily occluded for varying reasons or alternatively joined together. Consequently, even without any modification, the clamp may have potential use outside of "off pump CAGS". Size or other minor changes to the design, may allow an even broader range of applications for the clamp for other surgical procedures on humans or on animals.

The embodiments have been described by way of example only and modifications are possible within the scope of the invention.

The invention claimed is:

1. A clamp for surgical use, the clamp comprising a pair of arms pivotally interconnected at adjacent ends for pivotal movement in a plane between an open configuration in which the arms define a V-shaped configuration and a closed configuration in which the arms are approximately parallel, and a ratchet device located generally opposite of the interconnection of the arms and operative during closing movement to retain the arms in a selected, closed condition, wherein each arm has a clamping member in the form of a post located on the arm between the interconnection of the arms and the ratchet device and extending therefrom substantially perpendicularly to the plane of pivotal movement whereby distal ends of the posts extend outside of the plane, each of the two posts having a clamping face whereby an artery can be clamped between the respective clamping faces of the two posts as the arms are moved to the closed configuration.

2. A clamp according to claim 1, wherein the clamping faces are each inclined relative to the axis of the post by an angle of approximately 4° to 6° so as to converge at an included angle of approximately 8° to 12°.

3. A clamp according to claim 1, wherein the clamping faces of the clamping posts converge in a direction towards the distal ends of the posts.

4. A clamp according to claim 3, wherein the clamping faces are of substantially planar form.

5. A clamp according to claim 4, wherein the clamping posts are each of a tapered shape, narrowing towards its distal end.

6. A clamp according to claim 4, wherein the clamp is formed as a one-piece plastics moulding with the pivot being formed by a hinge consisting of a flexible web of plastics material interconnecting the adjacent ends of the two arms, and the ratchet device is formed by interengageable ratchet teeth formed on the respective arms, the teeth being disengageable to release the clamp by flexing movement permitted by the inherent flexibility of the plastics material from which the clamp is formed.

7. A clamp for surgical use, the clamp comprising a pair of arms pivotally hinged at adjacent ends for pivotal movement in a plane between an open configuration in which the arms define a V-shaped configuration and a closed configuration in which the arms are approximately parallel, and a ratchet device spaced from the hinge and operative during closing movement to retain the arms in a selected, closed, condition, wherein each arm has a clamping member in the form of a post having a clamping face, wherein each post is positioned between the hinge and the ratchet device and extends from the arm substantially perpendicularly to the said plane of pivotal movement whereby the posts with their clamping faces extend beneath the arms whereby an artery lying beneath the arms can be clamped between the clamping faces of the two posts as the arms are moved to their closed position.

8. A surgical clamp comprising:

a pair of arms connected at a hinge located at a first end of said clamp, said arms pivotally movable in a plane between an open configuration in which said arms define a V-shaped configuration and a closed configuration in which said arms are approximately parallel;

a ratchet device located at a second end of said clamp generally opposite said hinge, said ratchet device operable during closing movement of said arms to retain said arms in a selected, closed, condition;

said arms each including a clamping member comprising a post having a clamping face and extending from said arm substantially perpendicularly to said plane, said post located intermediate said hinge and said ratchet; and wherein a vessel can be clamped between the respective clamping faces of said posts as said arms are moved to their closed position.

* * * * *